(12) United States Patent
Rautschek et al.

(10) Patent No.: US 8,729,183 B2
(45) Date of Patent: May 20, 2014

(54) SILICONE EMULSIONS AND METHOD FOR PRODUCING SAME

(75) Inventors: Holger Rautschek, Nuenchritz (DE); Gerhard Beer, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/979,432

(22) PCT Filed: Jan. 9, 2012

(86) PCT No.: PCT/EP2012/050202
§ 371 (c)(1),
(2), (4) Date: Jul. 12, 2013

(87) PCT Pub. No.: WO2012/095374
PCT Pub. Date: Jul. 19, 2012

(65) Prior Publication Data
US 2013/0309283 A1    Nov. 21, 2013

(30) Foreign Application Priority Data

Jan. 13, 2011    (DE) .......................... 10 2011 002 668

(51) Int. Cl.
*C08L 83/06* (2006.01)
*C08G 77/16* (2006.01)

(52) U.S. Cl.
USPC ........... 524/837; 524/706; 524/710; 524/755; 524/759; 524/760

(58) Field of Classification Search
None
See application file for complete search history.

(56) References Cited

U.S. PATENT DOCUMENTS

| 3,294,725 A | 12/1966 | Findlay et al. |
| 3,634,285 A | 1/1972 | Brooks |
| 4,194,988 A | 3/1980 | Schneider et al. |
| 4,476,282 A | 10/1984 | Koerner et al. |
| 4,600,436 A | 7/1986 | Traver et al. |
| 7,745,533 B2 * | 6/2010 | Paul .............................. 524/837 |
| 8,580,862 B2 * | 11/2013 | Barnes et al. ................... 516/55 |
| 2008/0033062 A1 | 2/2008 | Herzig et al. |
| 2008/0064813 A1 | 3/2008 | Schneider |
| 2012/0171147 A1 | 7/2012 | Rautschek |

FOREIGN PATENT DOCUMENTS

| DE | 1495512 | 4/1970 |
| DE | 2014174 | 10/1970 |
| DE | 2730923 | 1/1979 |
| DE | 10 2004 038 148 A1 | 3/2006 |
| DE | 102005022099 A1 | 11/2006 |
| EP | 0093310 A2 | 11/1983 |
| EP | 1368109 | 12/2003 |
| EP | 1072629 A2 | 1/2011 |
| JP | 2001288269 A | 10/2001 |
| JP | 2002020490 A | 1/2002 |
| WO | 02070112 A2 | 9/2002 |
| WO | 2006015740 A1 | 2/2006 |
| WO | 2006102010 A1 | 9/2006 |
| WO | 2011032824 A1 | 3/2011 |

OTHER PUBLICATIONS

Xiaowen Guo et al, "Calculation of hydrophile-lipophile balance for polyethoxylated surfactants by group contribution method", Journal of Colloid and Interface Science, 298 (2006), pp. 441-450, Elsevier, Inc.

* cited by examiner

*Primary Examiner* — Marc Zimmer
(74) *Attorney, Agent, or Firm* — Brooks Kushman P.C.

(57) ABSTRACT

Aqueous emulsions of high viscosity organopolysiloxanes can be prepared having a very low content of cyclic siloxanes by condensing low molecular weight alkoxy-functional organopolysiloxanes in aqueous emulsion with an alkylphosphate emulsifier and at least one selected polyoxyethylene nonionic surfactant.

15 Claims, No Drawings

SILICONE EMULSIONS AND METHOD FOR PRODUCING SAME

CROSS-REFERENCE TO RELATED APPLICATIONS

This application is the U.S. National Phase of PCT Appln. No. PCT/EP2012/050202 filed Jan. 9, 2012 which claims priority to German Application No. 10 2011 002 668.1 filed Jan. 13, 2011, the disclosures of which are incorporated in their entirety by reference herein.

BACKGROUND OF THE INVENTION

1. Field of the Invention

The invention relates to aqueous silicone emulsions which comprise high-viscosity polyorganosiloxanes and have a particularly low content of cyclic siloxanes, to processes for preparation thereof and to the use thereof.

2. Description of the Related Art

Silicones have a variety of uses. In order to facilitate application and metering, particularly in the case of viscous products, it is desirable for many applications that the organosilicon compounds are in dilute form. The use of organic solvents such as benzene or hydrochlorocarbons is possible for this purpose, but disadvantageous from an ecological and occupational health point of view. Therefore, use is usually effected in the form of aqueous emulsions or dispersions, typically in the form of oil-in-water emulsions (O/W emulsions) which can be diluted with water. The oil phase here is understood to mean the water-immiscible organosilicon compounds, optionally dissolved in organic solvents. For many uses, it is advantageous when the silicone has a high molecular weight and hence a high viscosity. A known way of arriving at emulsions comprising a high molecular weight silicone is the emulsion polymerization of low molecular weight, especially cyclic, organosiloxanes with arylalkylsulfonic acids (DE-A 14 95 512). In this context, through vigorous stirring or homogenization with a high-pressure homogenizer, exceptionally low particle sizes are achieved, these no longer being perceptible with an optical microscope. A disadvantage of this process is the fact that, because of the equilibrium character of this reaction, more than 10% volatile cyclic siloxanes are present based on siloxane, but are undesirable. It has therefore been proposed that these be distilled off subsequently (e.g. U.S. Pat. No. 4,600,436) or removed by a membrane process (EP-A 1 368 109). Both processes mean additional technical complexity and can impair the stability of the emulsion.

Alternatively, rather than cyclic siloxanes, linear oligomers having terminal silanol groups can be used. These oligomers, in the presence of emulsifiers, condensation catalysts and a very small amount of water, form a paste in which the polycondensation takes place. Subsequently, this paste is diluted to the desired concentration (EP 93 310 B2). In general, the proportions of cyclic volatile siloxanes are lower than in the case of emulsion polymerization of cyclic siloxanes. The proportion of these volatile siloxanes can be reduced, for example, by first producing an emulsion from the salt form of the anionic emulsifier/catalyst, then activating this emulsion by adding acid (EP-A 1 072 629). This ultimately increases the salt content in the emulsion, which is disadvantageous for stability. In the case of use of alkoxy-terminated siloxane oligomers, it is said that less cyclic siloxanes are likewise formed (JP-A2001288269). However, the production of these oligomers is more complex and hence more costly.

Specific emulsifiers based on taurocholates likewise make a contribution to the reduction in the amount of cyclic products which are formed in the emulsion condensation of siloxane oligomers (WO 2006102010). Here too, as the working examples clearly show, more than 1% octamethylcyclotetrasiloxane is formed.

There have also been suggestions of emulsifying dimethylpolysiloxanes, especially polysiloxanes terminated with trimethylsiloxy groups, having viscosities of up to 5,000,000 cSt, by mixing and heating them with 10-30% of a phosphoric partial ester based on siloxane until a clear solution has formed, which, after neutralization, is diluted with water (DE-A 27 30 923). However, this process has the disadvantage that the polydimethylsiloxane is usually depolymerized in the process, and so the emulsion obtained contains a low-viscosity siloxane and a high proportion of volatile cyclic siloxanes, e.g. octamethylcyclotetrasiloxane.

JP2002020490 proposes using, as emulsifiers, at least one two-substance combination of polyoxyethylene alkyl sulfates, polyoxyethylene alkyl phosphates and alkylsulfonates, or the corresponding acids, it being preferable that the acid is released in the emulsion only through addition of mineral acids such as sulfuric acid. Sole use of polyoxyethylene alkyl phosphates is said to lead only to low molecular weight polyorganosiloxanes, since the catalytic activity thereof is too low. Therefore, combinations with sulfates or sulfonates and activation of sulfuric acid are necessary. This ultimately leads in turn to more than 1% cyclic siloxane oligomers, unless the reaction time is extremely short, in which case, however, viscosities of >1,000,000 mm²/s are not achieved.

On the other hand, such emulsions are often produced practically in such a way that either several batches are produced batchwise and transferred into a maturing tank, or a continuous campaign is produced over a particular period in a maturing tank, where the reaction is stopped by neutralization after attainment of the desired viscosity. In this case, it is unavoidable that a considerable proportion of the emulsion resides in the tank for longer than required, as a result of which the proportion of cyclic oligomers exceeds the tolerable extent.

SUMMARY OF THE INVENTION

The invention provides emulsions of polyorganosiloxanes comprising (A) polyorganosiloxanes having a viscosity greater than 10,000 mm²/s, measured at 25° C., (B) at least one emulsifier of the formula $$(RO)_n P(O)(OH)_{(3-n)} \qquad (I),$$

in which

R may be the same or different and denotes monovalent hydrocarbyl radicals having 4 to 30 carbon atoms, n is 1 or 2, and/or salts thereof, (C) at least one second emulsifier selected from the group consisting of (C1) ethoxylated triglycerides having 40 to 400 ethylene glycol groups, (C2) ethoxylated sorbitan esters of fatty acids having 12 to 18 carbon atoms and 10 to 40 ethylene glycol groups, (C3) compounds of the formula $$R^1 - O - (CH_2CH_2O)_m - H \qquad (II)$$

and (C4) compounds of the formula $$R^2 CH_2 C(O) - O - (CH_2CH_2O)_p - H \qquad (III),$$

in which
R¹ is an alkyl radical having 10 to 30 carbon atoms,
R² is an alkyl radical having 10 to 30 carbon atoms,
m is from 15 to 100 and
p from 15 to 100,
and
(D) water,
with the proviso that the emulsions contain less than 2% by weight of octaorganylcyclotetrasiloxane ($D_4$), based on component (A).

The invention further provides a process for producing the inventive emulsions, characterized in that
(a) polyorganosiloxanes containing units of the general formula $$R^4{}_a(R^3O)_b SiO_{(4-a-b)/2} \quad (IV),$$

in which
R⁴ may be the same or different and is a monovalent, optionally substituted hydrocarbyl radical having 1 to 30 carbon atoms or hydrogen atom,
R³ may be the same or different and is a hydrogen atom or a monovalent, optionally substituted hydrocarbyl radical,
a is 0, 1, 2 or 3 and
b is 0, 1, 2 or 3,
with the proviso that the sum of a+b is less than or equal to 3, and the polyorganosiloxanes contain 5 to 500 units of the formula (IV), where b is not 0 in at least one unit,
(b) emulsifier of the formula (I), wherein the OH groups may optionally be partly neutralized,
(c) emulsifier selected from the group consisting of ethoxylated triglycerides having 40 to 400 ethylene glycol groups, ethoxylated sorbitan esters of fatty acids having 12 to 18 carbon atoms and 10 to 40 ethylene glycol groups, compounds of the formula (II) and compounds of the formula (III),
(d) water and
optionally
(e) further substances
are mixed by stirring and/or homogenizing, and the organopolysiloxanes (a) containing units of the formula (IV) are allowed to condense at temperatures of 0 to 50° C. until the desired viscosity has been attained and then the emulsifier of the formula (I) is optionally neutralized with bases, such that the pH of the emulsion is greater than 5, and optionally further water (d) and/or further substances (e) are added.

DETAILED DESCRIPTION OF THE PREFERRED EMBODIMENTS

The inventive emulsions can be produced by processes known to those skilled in the art.

Mixing and homogenizing tools used may be all emulsifying units known to those skilled in the art, for example high-speed stirrers, dissolver disks, rotor-stator homogenizers, ultrasound homogenizers and high-pressure homogenizers of various designs. The process according to the invention can be operated continuously, semicontinuously or batchwise.

A preferred embodiment of the process according to the invention is characterized in that
in a 1st step
(a) 100 parts by weight of polyorganosiloxanes containing units of the general formula $$R^4{}_a(R^3O)_b SiO_{(4-a-b)/2} \quad (IV),$$

in which
R⁴ may be the same or different and is a monovalent, optionally substituted hydrocarbyl radical having 1 to 30 carbon atoms or hydrogen atom,
R³ may be the same or different and is a hydrogen atom or a monovalent, optionally substituted hydrocarbyl radical,
a is 0, 1, 2 or 3 and
b is 0, 1, 2 or 3,
with the proviso that the sum of a+b is less than or equal to 3, and the organopolysiloxanes contain 5 to 500 units of the formula (IV), where b is not 0 in at least one unit,
(b) 1 to 30 parts by weight of an emulsifier of the formula (I), wherein the OH groups may optionally be partly neutralized,
(c) 1 to 30 parts by weight of an emulsifier selected from the group consisting of ethoxylated triglycerides having 40 to 400 ethylene glycol groups, ethoxylated sorbitan esters of fatty acids having 12 to 18 carbon atoms and 10 to 40 ethylene glycol groups, compounds of the formula (II) and compounds of the formula (III),
(d) 1 to 50 parts by weight of water and
optionally
(e) further substances
are mixed by stirring and/or homogenizing;
in an optional 2nd step
further water (d) is added;
in a 3rd step
the organopolysiloxanes (a) containing units of the formula (IV) are allowed to condense at temperatures of 0 to 50° C. until the desired viscosity has been attained;
in an optional 4th step
the emulsifier of the formula (I) is neutralized with bases, such that the pH of the emulsion is greater than 5; and
in an optional 5th step
the emulsion obtained in the 4th step is mixed with further water (d) and/or further substances (e).

The polyorganosiloxanes (A) present in the inventive emulsions are preferably those containing units of the formula (IV), more preferably those composed of units of the formula (IV) with an average value of a of 1.990 to 2.005 and an average value of b of 0.001 to 0.004, especially those composed of units of the formula (IV) where R³ is a hydrogen atom, R⁴ is a methyl radical and an average value of a is 1.990 to 2.005 and an average value of b is 0.001 to 0.004. Most preferably, the polyorganosiloxanes (A) are dimethylpolysiloxanes bearing trimethylsiloxy and/or dimethylhydroxysiloxy end groups.

Polyorganosiloxanes (A) present in the inventive emulsions preferably have a viscosity of greater than 100,000 mm²/s, more preferably greater than 1,000,000 mm²/s, in each case at 25° C.

Examples of R radicals are branched or unbranched alkyl radicals having 4 to 30 carbon atoms, such as butyl, hexyl, 2-ethylhexyl, octyl, isononyl, n-decyl, dodecyl, isotridecyl and n-tetradecyl radicals, unsaturated aliphatic radicals such as oleyl radicals, and aromatic radicals such as phenyl, toluyl, xylyl, nonylphenyl, naphthyl, anthracyl, tristyrylphenyl or benzyl radicals.

Preferably, the R radical comprises alkyl radicals having 4 to 18 carbon atoms, more preferably n-butyl, n-octyl, 2-ethylhexyl, n-decyl, n-dodecyl or n-tetradecyl radicals, especially n-octyl and n-decyl radicals.

Examples of compounds of the formula (I) used in accordance with the invention are di-n-butyl phosphate, di-n-hexyl phosphate, mono-n-octyl phosphate, di-n-octyl phosphate, mono-2-ethylhexyl phosphate, di-2-ethylhexyl phosphate, mono-i-nonyl phosphate, di-i-nonyl phosphate, mono-n-decyl phosphate, n-octyl n-decyl phosphate, di-n-decyl phosphate, monoisotridecyl phosphate, di-n-nonylphenyl phosphate, monooleyl phosphate and distearyl phosphate.

Preferably, the compounds of the formula (I) used in accordance with the invention are mono-n-octyl phosphate, di-n-octyl phosphate, mono-n-decyl phosphate, n-octyl-n-decyl phosphate and di-n-decyl phosphate.

Preferably, the compounds of the formula (I) used in accordance with the invention are mixtures of diesters and monoesters.

The inventive emulsions may comprise, as component (B), compounds of the formula (I) as such or salts thereof, preferably with alkali metal or alkaline earth metal hydroxides, ammonia or amines, or mixtures of acids of the formula (I) and salts thereof.

Component (B) of the inventive emulsions preferably comprises salts of the compounds of the general formula (I), especially alkali metal salts or triethanolamine salts.

The acid number of component (B) present in the inventive emulsion is determined by the number of free OH groups therein and the molar mass thereof, i.e. the amount of KOH in mg which is required for neutralization of 1 g of component (B). The acid number of component (B) is preferably in the range from 0 to 200, more preferably in the range from 0 to 20, especially 0, i.e. the inventive emulsions in this case contain, as component (B), fully neutralized compounds of the formula (I).

Compounds of the formula (I) are commercially available or preparable by commonly known chemical methods.

The inventive emulsions comprise, as a further emulsifier (C), at least one nonionic emulsifier selected from compounds of the formulae (II) and (III), ethoxylated triglycerides or ethoxylated sorbitan esters.

Examples of $R^1$ and $R^2$ radicals are each independently the n-decyl, n-dodecyl, n-tetradecyl, n-hexadecyl, n-octadecyl and the n-octadecenyl radical.

The $R^1$ radical preferably comprises alkyl radicals having 12 to 20 carbon atoms, more preferably linear alkyl radicals. The alkyl radical $R^1$ especially has an even number of carbon atoms.

The $R^2$ radical preferably comprises alkyl radicals having 12 to 20 carbon atoms, more preferably linear alkyl radicals. The alkyl radical $R^2$ especially has an even number of carbon atoms.

Preferably, m has a value of 20 to 40.

Preferably, p has a value of 20 to 50.

Examples of ethoxylated triglycerides having 40 to 400 ethylene glycol groups (C1) are
ethoxylated castor oil having 200 ethylene glycol units, ethoxylated castor oil having 40 ethylene glycol units and ethoxylated hydrogenated castor oil having 200 ethylene glycol units.

Examples of ethoxylated sorbitan esters of fatty acids having 12 to 18 carbon atoms and 10 to 40 ethylene glycol groups (C2) are
polyoxyethylene(20) sorbitan stearate (Polysorbate® 60), polyoxyethylene(20) sorbitan tristearate (Polysorbate® 65), polyoxyethylene(20) sorbitan oleate (Polysorbate® 80) and polyoxyethylene(20) sorbitan laurate (Polysorbate® 20).

Examples of compounds (C3) of the formula (II) are
$C_{18}H_{37}-O-(CH_2CH_2O)_{20}-H$,
$C_{18}H_{35}-O-(CH_2CH_2O)_{20}-H$ and
$C_{12}H_{23}-O-(CH_2CH_2O)_{23}-H$.

Examples of compounds (C4) of the formula (III) are
$C_{16}H_{33}-CH_2-C(O)-O-(CH_2CH_2O)_{20}-H$,
$C_{16}H_{33}-CH_2-C(O)-O-(CH_2CH_2O)_{30}-H$,
$C_{16}H_{33}-CH_2-C(O)-O-(CH_2CH_2O)_{40}-H$ and $C_{16}H_{33}-CH_2-C(O)-O-(CH_2CH_2O)_{100}-H$.

Preferably, the emulsifier (C) present in the inventive emulsion has an HLB value greater than 14, more preferably greater than 15.5, especially 16.5 to 20. The HLB value is the expression of the equilibrium between hydrophilic and hydrophobic groups of an emulsifier. The definition of the HLB value and processes for determination thereof are known to those skilled in the art and are described, for example, in Journal of Colloid and Interface Science 298 (2006) 441-450 and the literature cited therein, especially citation [23].

Preferably, emulsifier (C) is a compound of the formula (II).

In addition to components (A), (B), (C) and (D), the inventive emulsions may comprise all further substances which are typically added to silicone emulsions, for example further siloxanes different than component (a), silanes, especially alkoxysilanes, further emulsifiers different than components (b) and (c), thickeners and/or protective colloids, and also additives, for example preservatives, disinfectants, wetting agents, corrosion inhibitors, dyes and fragrances.

The inventive emulsions are preferably those which comprise component (A) to an extent of preferably 1 to 80% by weight, more preferably to an extent of 20 to 70% by weight, component (B) to an extent of preferably 0.2 to 20% by weight, more preferably to an extent of 1 to 10% by weight, and
component (C) to an extent of preferably 0.2 to 20% by weight, more preferably to an extent of 1 to 10% by weight.

The inventive emulsions advantageously comprise only a very low proportion, if any, of cyclic siloxanes, especially of octaorganylcyclotetrasiloxanes ($D_4$). The organyl groups in the cyclosiloxanes correspond to the organyl groups in the organopolysiloxane used and are preferably methyl groups.

The inventive emulsion preferably contains preferably less than 1% by weight, more preferably less than 0.5% by weight, and especially less than 0.1% by weight, of octaorganylcyclotetrasiloxanes, especially octamethylcyclotetrasiloxane ($D_4$), based in each case on component (A).

The inventive emulsion preferably has a particle diameter of preferably 50 to 1000 nm, more preferably from 100 to 500 nm, especially from 100 to 200 nm, these figures being based on the mean of the volume distribution measured by the principle of Fraunhofer diffraction (according to ISO 13320).

The inventive emulsions have a content of nonvolatile components measured according to DIN EN ISO 3251 of preferably 1 to 80% by weight, more preferably 10 to 65% by weight, especially 30 to 60% by weight.

The pH of the inventive emulsion is preferably 5 to 10, more preferably 6 to 8, and especially about 7.

Examples of hydrocarbyl radicals $R^4$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl radical and methylcyclohexyl radicals; alkenyl radicals such as the vinyl, 1-propenyl and 2-propenyl radical; aryl radicals such as the phenyl, naphthyl, anthryl and phenanthryl radicals; alkaryl radicals such as the o-, m-, p-tolyl radicals, xylyl radicals and ethylphenyl radicals; and aralkyl radicals such as the benzyl radical, and the α- and β-phenylethyl radicals.

Examples of substituted R⁴ radicals are radicals substituted by halogen, cyano, glycidoxy, polyalkylene glycol or amino groups, for example trifluoropropyl, cyanoethyl, glycidoxypropyl, polyalkylene glycol propyl, aminopropyl or aminoethylaminopropyl radicals.

Preferably, not more than one R⁴ radical in the units of the formula (IV) is a hydrogen atom.

Preferably, the R⁴ radical comprises hydrocarbyl radicals having 1 to 18 carbon atoms, more preferably the methyl or phenyl radicals, and especially more than 80 mol % of the R⁴ radicals in the siloxane (a) are methyl radicals.

Examples of R³ radicals are the examples given for R⁴ radicals. Preferably, the R³ radical is a hydrogen atom or a hydrocarbyl radical having 1 to 4 carbon atoms, more preferably a hydrogen atom.

In formula (IV), the sum of a+b preferably has a value of on average 1.5 to 2.4, more preferably on average 1.8 to 2.3, and especially 1.9 to 2.1.

The siloxanes (a) used in the process of the invention consist preferably of 5 to 500, more preferably 10 to 200, and especially 20 to 100 units of the formula (IV).

In preferably 0.4 to 40%, more preferably 2 to 10%, of the units of the formula (IV) in the siloxanes (a) used in the process according to the invention, b is not 0.

Examples of siloxanes (a) used in accordance with the invention are polydiorganosiloxanes terminated with alkoxy or hydroxyl groups, especially polydiethyl- and polydimethylsiloxanes.

The siloxanes (a) used in the process according to the invention preferably have a viscosity of 5 to 10 000 mm²/s, more preferably 10 to 500 mm²/s, and especially 30 to 100 mm²/s, in each case at 25° C.

Preferably, the siloxanes (a) are those of the formula

$$HO[SiR^4{}_2O]_c\text{—}H \quad (V)$$

where R⁴ has one of the abovementioned meanings, especially a methyl radical, and c has a value of 5 to 500, preferably 10 to 200, and more preferably from 20 to 100.

The polysiloxanes (a) containing units of the formula (IV) are commercial products or can be prepared by known processes.

Examples of component (b) are the abovementioned examples for the compounds of the formula (I), optionally in a mixture with salts thereof.

The acid number of the compound of the formula (I) used in the process according to the invention is determined by the average value of n and the molar mass thereof, i.e. the amount of KOH in mg which is required for neutralization of 1 g of compound of the formula (I). The acid number of the compound of the formula (I) used in accordance with the invention is preferably in the range from 100 to 600, more preferably in the range from 200 to 500, and especially in the range from 250 to 450.

Component (b) is preferably used in the process according to the invention in amounts of 1 to 25 parts by weight, especially 2 to 10 parts by weight, based in each case on 100 parts by weight of polyorganosiloxane (a).

Examples of component (c) are the abovementioned examples for the compounds (C).

Component (c) is preferably used in the process according to the invention in amounts of 1 to 25 parts by weight, especially 5 to 20 parts by weight, based in each case on 100 parts by weight of polyorganosiloxane (a).

The water (d) may be any of water which is useful for production of dispersions.

The water (d) is preferably partly or fully demineralized water, distilled or (repeatedly) redistilled water, water for medical or pharmaceutical purposes, for example purified water (aqua purificata according to Pharm. Eur.).

The water (d) used in accordance with the invention preferably has a conductivity of less than 50 μS/cm, more preferably less than 10 μS/cm, and especially less than 1.3 μS/cm, in each case at 25° C. and 1010 hPa.

Water (d) is preferably used in the process according to the invention in amounts of 20 to 1000 parts by weight, especially 30 to 400 parts by weight, based in each case on 100 parts by weight of polyorganosiloxane (a). In the preferred process variant, water is added in the first step, in the optional second step and in the optional fifth step, preferably using water in the first step of the process in amounts of 1 to 30 parts by weight, especially 5 to 20 parts by weight, based in each case on 100 parts by weight of polyorganosiloxane (a).

In addition to components (a), (b), (c) and (d), all further substances (e) which are typically added to silicone emulsions can be used in the process according to the invention, for example further siloxanes different than component (a), silanes, especially alkoxysilanes, further emulsifiers different than components (b) and (c), thickeners and/or protective colloids, and also additives, for example preservatives, disinfectants, wetting agents, corrosion inhibitors, dyes and fragrances. The addition of these components (e) can be effected in the first step of the process according to the invention and/or else in a later process step, for example after the 5th step.

Examples of further siloxanes (e) which can be used in accordance with the invention are those of the formula (IV) where b is 0, for example trimethylsiloxy-terminated polydimethylsiloxanes. Such siloxanes (e) are advantageously used to control the viscosity of the polysiloxane obtained after the condensation reaction in the emulsion.

If further siloxanes (e) are used, the amounts are preferably 0.01 to 10 parts by weight, based on 100 parts by weight of component (a). In the process according to the invention, preferably no further siloxanes (e) are used.

Examples of silanes (e) which can be used in accordance with the invention are methyltrimethoxysilane, tetraethoxysilane, vinyltriethoxysilane, morpholinomethyltriethoxysilane, cyclohexylaminomethylmethyldiethoxysilane, the examples cited in DE-A 102005022099, paragraph [0052] and in DE-A 102004038148, paragraph [0033], or the hydrolysis/condensation products thereof. Such silanes (e) are advantageously used to obtain branched or crosslinked siloxanes, for example those which form elastic films after the drying of the emulsion. In the preferred process variant, these silanes (e) can be added in the 1st step, or else after the 3rd step.

If silanes (e) are used, the amounts are preferably 0.01 to 10 parts by weight, based on 100 parts by weight component (a). In the process according to the invention, preferably no silanes (e) are used.

Examples of further emulsifiers (e) which can be used in accordance with the invention are all emulsifiers known to date, such as anionic or nonionic emulsifiers, for example alkyl sulfates, ethoxylated alkyl sulfates, and polyethylene glycol ethers of alkylphenols and alkyl polyglycosides.

In the process according to the invention, preferably no cationic and no amphoteric emulsifiers are used.

In the process according to the invention, preferably no further anionic emulsifiers, more particularly no alkyl- or alkylarylbenzenesulfonic acids or salts thereof, are used as component (e).

If further emulsifiers (e) are used, the amounts are preferably 1 to 20 parts by weight, based on 100 parts by weight component (a).

Preferably, no further emulsifiers are used as component (e).

If thickeners or protective colloids are used as component (e) in the process according to the invention, these are preferably acrylic acid copolymers.

If thickeners and/or protective colloids (e) are used, the amounts are preferably 0.01 to 2 parts by weight, based on 100 parts by weight component (a). In the process according to the invention, preferably no thickener and/or protective colloid (e) is used.

Examples of additives (e) which can be used in accordance with the invention are, for example, preservatives, dyes or fragrances known to those skilled in the art, especially preservatives such as methylisothiazolinone, chloromethylisothiazolinone, benzylisothiazolinone, phenoxyethanol, methylparaben, ethylparaben, propylparaben, butylparaben, isobutylparaben, alkali metal benzoates, alkali metal sorbates, iodopropinyl butylcarbamate, benzyl alcohol and 2-bromo-2-nitropropane-1,3-diol.

If additives (e) are used, the amounts are preferably 0.0005 to 2 parts by weight, based on 100 parts by weight of component (a). In the process according to the invention, preference is given to using additives (e).

In the first step of the preferred embodiment of the process according to the invention, all components can be mixed with one another by stirring and/or homogenizing, for example in any sequence, the peripheral speed of the stirrer and/or rotor-stator homogenizer preferably being greater than 5 m/s, more preferably greater than 10 m/s, and especially 5 to 50 m/s.

Compounds of the formula (I) as component (b) can, if desired, be partly neutralized as early as in the first step of the process according to the invention with bases, for example alkali metal hydroxides or amines, but this is not preferred.

The mixture according to a first step of the process according to the invention has a pH of less than 6, preferably less than 5, more preferably less than 4, and especially 1 to 3.

Preferably, the emulsion composed of components (a), (b), (c), (d) and optionally (e) obtained in the first step is highly viscous and not free-flowing. It is especially preferable when the yield point (according to DIN 53019-1 and cited standards) of the emulsion obtained in the first step is greater than 100 Pa, especially greater than 1000 Pa.

The first step of the process according to the invention is preferably performed at temperatures of preferably 5 to 80° C., especially 10 to 50° C., and at the pressure of the surrounding atmosphere, i.e. between 900 and 1100 hPa, or at an elevated pressure of up to 20,000 hPa, especially up to 10,000 hPa.

Preferably, the duration of the first step of the invention is less than 4 hours, more preferably less than 2 hours, and especially 5 to 60 minutes.

The mixture obtained in the first step of the process according to the invention preferably has a particle size (mean of the volume distribution) of less than 1 pm, more preferably 100 to 500 nm, and especially 100 to 200 nm.

In the optional second step of the process according to the invention, the emulsion obtained in the first step, especially when it is highly viscous to firm, is diluted with water with stirring and/or homogenization, so as to form a free-flowing emulsion which preferably contains more than 50 parts water per 100 parts component (a).

The stirring or homogenizing can be effected under the same conditions as described for the first step.

The second step of the process according to the invention is preferably performed at temperatures of preferably 5 to 50° C., especially 10 to 30° C., and at the pressure of the surrounding atmosphere, i.e. between 900 and 1100 hPa, or at an elevated pressure of up to 20,000 hPa, especially of up to 10,000 hPa.

The second step can be effected in the same vessel as the first process step.

Preferably, the duration of the second step in accordance with the invention, which is optional, is less than 4 hours, more preferably less than 2 hours, and especially 5 to 60 minutes.

In the process according to the invention, the second step is preferably performed.

In the third step of the process according to the invention, the organopolysiloxanes (a) are allowed to condense until the viscosity as desired for siloxane (A) in the inventive emulsion has been attained, i.e. a viscosity of greater than 10,000 mm$^2$/s, preferably greater than 100,000 mm$^2$/s, more preferably greater than 1,000,000 mm$^2$/s, in each case at 25° C.

Preferably, the duration of the third step of the invention is 1 to 200 hours, more preferably 8 to 96 hours, especially 12 to 72 hours. The third step can be effected in the same vessel as the first and second steps. However, the emulsion can also be transferred to a special vessel where, if appropriate, several batches produced in succession are mixed for the third step. However, it is also possible to perform the first and second steps continuously and the third step in a maturing tank.

The third step of the process according to the invention is preferably performed at temperatures of 2 to 50° C., more preferably 5 to 30° C., especially at 5 to 20° C., and a pressure of the surrounding atmosphere, i.e. between 900 and 1100 hPa.

Any alcohols obtained as condensation by-products in the process according to the invention, for example when $R^3$ in formula (IV) is not a hydrogen atom, may remain in the emulsion or else be removed, for example by distillation under reduced pressure or by extraction.

Examples of the bases used in the optional fourth step of the process according to the invention are alkali metal hydroxides such as NaOH and KOH, and amines, for example monoethanolamine and triethanolamine. The pH can in principle also be adjusted by the addition of alkali metal salts of weak acids, for example sodium citrate, sodium silicate, potassium acetate or potassium phosphate.

Preferably, the bases which can be used in the fourth step of the process according to the invention are alkali metal or alkaline earth metal hydroxides, ammonia and amines, more preferably NaOH, KOH, monoethanolamine and triethanolamine.

The pH of the emulsion after the inventive neutralization is preferably 5 to 10, more preferably 6 to 8, and especially about 7.

The optional fourth step of the process according to the invention is preferably performed at temperatures of 5 to 50° C., more preferably 15 to 30° C., and a pressure of the surrounding atmosphere, i.e. between 900 and 1100 hPa.

In the process according to the invention, the fourth step is preferably performed.

The emulsions obtained in accordance with the invention can then be mixed in an optional 5th step with further water (d) and/or further substances (e) as desired.

Preferably, no further components are used in addition to components (a), (b), (c), (d) and optionally (e) and bases in the process according to the invention.

The components used in the process according to the invention may each be one kind of such a component, or else a mixture of at least two kinds of a particular component.

The inventive emulsions, or those produced in accordance with the invention, have the advantage that they comprise high-viscosity polydiorganosiloxanes and have a low content of cyclic siloxanes.

In addition, the inventive emulsions, or those produced in accordance with the invention, have the advantage that they are very stable and thus have a long shelf life.

The inventive emulsions, or those produced in accordance with the invention, have the advantage that they are storage-stable and have excellent performance properties, for example very good action as separating agents and lubricants, good wetting capacity in different substrates, good conditioning action in haircare products, i.e. distinct reduction in wet and dry combing force.

The process according to the invention has the advantage that it is possible to produce emulsions comprising high molecular weight siloxanes in a simple and inexpensive manner.

The process according to the invention also has the advantage that, even after a relatively long duration of the third step, the proportion of cyclic siloxanes remains low, which is particularly favorable, for example, in the case of continuous production with a relatively broad residence time range.

The process according to the invention has the advantage that the viscosity of the oil can be varied and adjusted in a simple manner within a wide range without forming an elevated proportion of cyclic siloxanes.

The inventive emulsions, or those produced in accordance with the invention are usable for all purposes for which emulsions comprising high-viscosity siloxanes are useful, for example as separating agents, lubricants, hydrophobizing agents, and for textile impregnation, in the processing of rubber and plastics or in metalworking, hydrophobizing agents for glass and mineral building materials, or as a constituent of personal care products.

In the case of use as a lubricant for sewing threads, the inventive emulsions can be combined, for example, with wax emulsions. The inventive emulsions can be used to produce separating agent formulations, for example for the tire industry, these comprising, as well as the inventive emulsion, further components such as thickeners, for example xantham gum or polyacrylates, fillers such as talc or mica, waxes and further components known to those skilled in the art. The high viscosity and the low content of volatile siloxanes is particularly advantageous in these applications.

The invention further provides personal care compositions comprising inventive emulsions in amounts of 0.05 to 10% by weight, more preferably 0.5 to 5% by weight.

The inventive personal care compositions are preferably haircare compositions.

These haircare compositions comprise, as well as the inventive emulsions, or those produced in accordance with the invention, preferably one or more conditioners selected, for example, from the group of quaternary ammonium compounds, natural or synthetic waxes, vegetable oils, mineral oils, fluorinated oils, silicone oils, especially aminosilicone oils, organic polymers and copolymers, which may be nonionic, anionic, cationic or amphoteric, cationic proteins and cationic surfactants.

Further constituents of these haircare compositions are, for example, water, surfactants, fatty alcohols, rheology modifiers, pearlizers, organic acids, fragrances, preservatives, vitamins, sunscreens, salts, dyes, and further components of haircare compositions known to those skilled in the art.

The haircare compositions comprising the inventive emulsions, or those produced in accordance with the invention, may, for example, be shampoos, hair masks, hair rinses, hair waxes, hair creams, hair gels, hair foams, hairsprays and hair colorants. These care compositions improve both the dry and wet combability, and also the feel of the wet and dry hair.

Application can be effected, for example, in the course of washing, after washing, as a pre- or aftertreatment in the course of bleaching or in the course of coloring with direct or oxidation dyes, and in the course of permanent shaping of the hair (e.g. permanent wave).

The invention further provides haircare compositions comprising inventive emulsions and at least one conditioner.

In the examples which follow, all figures for parts and percentages, unless stated otherwise, are based on weight.

Unless stated otherwise, the examples which follow are performed at a pressure of the surrounding atmosphere, i.e. at about 1010 hPa, and at room temperature, i.e. about 25° C., or a temperature which is established on combination of the reactants at room temperature without additional heating or cooling. All viscosity figures given in the examples are based on a temperature of 25° C.

The emulsions produced in the examples which follow were tested as follows:

The particle size was determined with a Malvern Zetasizer ZEN1600/Nano-S particle size analyzer, Software Version 6.01, by means of dynamic light scattering. For this purpose, the emulsions were diluted to 0.5% with filtered and degassed water. The values reported are always based on the D(50) value.

To determine the oil viscosity, 20 g of emulsion were admixed with 30 g of acetone, and the emulsion separated. The acetone/water phase was removed and the operation was repeated once more. Subsequently, the polymer was washed three times with water and dried at 110° C. while stirring until no water droplets were visible any longer, and then after-treated at 110° C. in a drying cabinet for another 8 h. The viscosity was determined with an MCR 300 cone-plate viscometer (Paar-Physika) at 25° C. and a shear gradient of 1/s.

To determine the content of octamethylcyclotetrasiloxane ($D_4$), a $^{29}Si$ NMR spectrum of the emulsion was recorded (Bruker Avance 400, 10 mm selective $^{29}Si$ NMR sample head, addition of 15% $D_2O$ to the original emulsion, pulse angle 30°, wait time 30 s, 400 scans).

The integrals of the signals between −19.75 and −20 ppm ($D_4$) and −21.5 to −23.25 (remaining D units) were used to determine the $D_4$ content in mol % of Si, and this, because of the equal molar mass of the individual siloxane unit (74 g/mol), is virtually equal to the proportion of $D_4$ in % by weight based on polydimethylsiloxanes.

EXAMPLE 1

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 10 parts of a 2-ethylhexyl phosphate having an acid number of 295 mg KOH/g (obtainable under the "Servoxyl VPTZ 100" name from Elementis Specialties Netherlands B.V. Delden), 14 parts of an ethoxylated stearyl alcohol of the formula $C_{18}H_{37}$—O—$(CH_2CH_2O)_{20}$—H obtainable under the "Arlypon SA 20" name from Cognis AG, Düsseldorf) and 10 parts of water are added and homogenized for 10 min. The gel-like phase formed (yield point 920 Pa) having a particle size of less than 250 nm is diluted with 100 parts of water within 10 min and stored at 10° C. This emulsion had a pH of 2.6. After 24 h, the emulsion is adjusted to a pH of 7 with triethanolamine, and 0.18 part of preservative based on isothiazolinones (obtainable under the "Kathon CG" name from Acima Chemical Industries Ltd., CH-9471 Buchs/SG) is added.

The emulsion thus obtained is then analyzed for particle size, oil viscosity and the content of octamethylcyclotetrasiloxane $D_4$. The results can be found in Table 1.

EXAMPLE 2

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 10 parts of an isononyl phosphate having an acid number of 300 mg KOH/g (obtainable under the "Servoxyl VPXZ 100" name from Elementis Specialties Netherlands B.V. Delden), 10 parts of an ethoxylated lauryl alcohol of the formula $C_{12}H_{23}$—O—$(CH_2CH_2O)_{23}$—H (obtainable under the "Brij 35" name from Croda GmbH, D-Nettetal) and 10 parts of water are homogenized for 5 min. The gel-like phase formed having a yield point of 1730 Pa and a particle size of less than 200 nm is diluted with 100 parts of water within 10 min and stored at 15° C. This emulsion had a pH of 2.3. After 24 h, the emulsion is adjusted to a pH of 7 with triethanolamine and 0.18 part of preservative based on isothiazolinones (obtainable under the "Kathon CG" name from Acima Chemical Industries Ltd., CH-9471 Buchs/SG) is added.

The emulsion thus obtained is then analyzed for particle size, oil viscosity and the content of octamethylcyclotetrasiloxane $D_4$. The results can be found in Table 1.

EXAMPLE 3

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 10 parts of a 2-ethylhexyl phosphate having an acid number of 295 mg KOH/g (obtainable under the "Servoxyl VPTZ 100" name from Elementis Specialties Netherlands B.V. Delden), 10 parts of an ethoxylated lauryl alcohol of the formula $C_{12}H_{23}$—O—$(CH_2CH_2O)_{23}$—H (obtainable under the "Brij 35" name from Croda GmbH, D-Nettetal) and 10 parts of water are added and homogenized for 10 min. The gel-like phase formed (yield point 1340 Pa) having a particle size of less than 200 nm is diluted with 100 parts of water within 10 min and stored at 10° C. This emulsion had a pH of 2.2. After 24 h, the emulsion is adjusted to a pH of 7 with triethanolamine and 0.18 part of preservative based on isothiazolinones (obtainable under the "Kathon CG" name from Acima Chemical Industries Ltd., CH-9471 Buchs/SG) is added.

The emulsion thus obtained is then analyzed for particle size, oil viscosity and the content of octamethylcyclotetrasiloxane $D_4$. The results can be found in Table 1.

EXAMPLE 4

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 6 parts of a 2-ethylhexyl phosphate having an acid number of 225 mg KOH/g (obtainable under the "Servoxyl VPDZ 100" name from Elementis Specialties Netherlands B.V. Delden), 10 parts of an ethoxylated lauryl alcohol of the formula $C_{12}H_{23}$—O—$(CH_2CH_2O)_{23}$—H (obtainable under the "Brij 35" name from Croda GmbH, D-Nettetal) and 10 parts of water are added and homogenized for 15 min. The gel-like phase formed (yield point 990 Pa) having a particle size of less than 200 nm is diluted with 100 parts of water within 10 min and stored at 10° C. This emulsion had a pH of 2.5. After 24 h, the emulsion is adjusted to a pH of 7 with triethanolamine and 0.18 part of preservative based on isothiazolinones (obtainable under the "Kathon CG" name from Acima Chemical Industries Ltd., CH-9471 Buchs/SG) is added.

The emulsion thus obtained is then analyzed for particle size, oil viscosity and the content of octamethylcyclotetrasiloxane $D_4$. The results can be found in Table 1.

EXAMPLE 5

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 4 parts of a n-butyl phosphate having an acid number of 465 mg KOH/g (obtainable under the "Servoxyl VPIZ 100" name from Elementis Specialties Netherlands B.V. Delden), 10 parts of an ethoxylated stearic acid of the formula $C_{16}H_{33}CH_2C(O)$—O—$(CH_2CH_2O)_{40}$—H (obtainable under the "Myrj 52S" name from Croda GmbH, D-Nettetal) and 10 parts of water are added and homogenized for 15 min. The gel-like phase formed (yield point 720 Pa) having a particle size of less than 200 nm is diluted with 100 parts of water within 10 min and stored at 10° C. This emulsion had a pH of 1.8. After 96 h, the emulsion is adjusted to a pH of 7 with triethanolamine and 0.18 part of preservative based on isothiazolinones (obtainable under the "Kathon CG" name from Acima Chemical Industries Ltd., CH-9471 Buchs/SG) is added.

The emulsion thus obtained is then analyzed for particle size, oil viscosity and the content of octamethylcyclotetrasiloxane $D_4$. The results can be found in Table 1.

EXAMPLE 6

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 10 parts of an octyl decyl phosphate having an acid number of 295 mg KOH/g (obtainable under the "Crodafos 810 A" name from Croda GmbH, D-Nettetal), 14 parts of an ethoxylated lauryl alcohol of the formula $C_{12}H_{23}$—O—$(CH_2CH_2O)_{23}$—H (obtainable under the "Brij 35" name from Croda GmbH, D-Nettetal) and 10 parts of water are added and homogenized for 10 min. The gel-like phase formed (yield point 1940 Pa) having a particle size of less than 200 nm is diluted with 100 parts of water within 10 min and stored at 10° C. This emulsion had a pH of 2.0. After 24 h, the emulsion is adjusted to a pH of 7 with triethanolamine and 0.18 part of preservative based on isothiazolinones (obtainable under the "Kathon CG" name from Acima Chemical Industries Ltd., CH-9471 Buchs/SG) is added.

The emulsion thus obtained is then analyzed for particle size, oil viscosity and the content of octamethylcyclotetrasiloxane $D_4$. The results can be found in Table 1.

EXAMPLE 7

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 6 parts of an octyl decyl phosphate having an acid number of 295 mg KOH/g (obtainable under the "Crodafos 810 A" name from Croda GmbH, D-Nettetal), 10 parts of an ethoxylated lauryl alcohol of the formula $C_{12}H_{23}O$—$(CH_2CH_2O)_{23}$—H (obtainable under the "Brij 35" name from Croda GmbH, D-Nettetal) and 10 parts of water are added and homogenized for 10 min. The gel-like phase formed (yield point 1110 Pa) having a particle size of less than 200 nm is diluted with 100 parts of water within 10 min and stored at 15° C. This emulsion had a pH of 2.1. After 24 h, the emulsion is adjusted to a pH of 7 with triethanolamine and 0.18 part of preservative based on isothiazolinones (obtainable under the "Kathon CG" name from Acima Chemical Industries Ltd., CH-9471 Buchs/SG) is added.

The emulsion thus obtained is then analyzed for particle size, oil viscosity and the content of octamethylcyclotetrasiloxane $D_4$. The results can be found in Table 1.

EXAMPLE 8

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 6 parts of an octyl decyl phosphate having an acid number of 295 mg KOH/g (obtainable under the "Crodafos 810 A" name from Croda GmbH, D-Nettetal), 10 parts of an ethoxylated sorbitan laurate (obtainable under the "Tween 20" name from Croda GmbH, D-Nettetal) and 10 parts of water are added and homogenized for 10 min. The gel-like phase formed (yield point 820 Pa) having a particle size of less than 300 nm is diluted with 100 parts of water within 10 min and stored at 15° C. This emulsion had a pH of 2.0. After 24 h, the emulsion is adjusted to a pH of 7 with triethanolamine and 0.18 part of preservative based on isothiazolinones (obtainable under the "Kathon CG" name from Acima Chemical Industries Ltd., CH-9471 Buchs/SG) is added.

The emulsion thus obtained is then analyzed for particle size, oil viscosity and the content of octamethylcyclotetrasiloxane $D_4$. The results can be found in Table 1.

EXAMPLE 9

100 parts of an α,ω-hydroxyl-terminated polydimethylsiloxane having a viscosity of 60 mPas are initially charged in a beaker. With a rotor-stator homogenizer (Ultra-Turrax, peripheral speed 16 m/s), 6 parts of an octyl decyl phosphate having an acid number of 295 mg KOH/g (obtainable under the "Crodafos 810 A" name from Croda GmbH, D-Nettetal), 10 parts of an ethoxylated castor oil (obtainable under the "Atlas G1300" name from Croda GmbH, D-Nettetal) and 10 parts of water are added and homogenized for 10 min. The gel-like phase formed (yield point 900 Pa) having a particle size of less than 200 nm is diluted with 100 parts of water within 10 min and stored at 15° C. This emulsion had a pH of 2.1. After 24 h, the emulsion is adjusted to a pH of 7 with triethanolamine and 0.24 part of preservative based on methylisothiazolinones and ethylhexylglycerol (obtainable under the "Euxyl K220" name from Schülke & Mayr GmbH, Norderstedt) is added.

The emulsion thus obtained is then analyzed for particle size, oil viscosity and the content of octamethylcyclotetrasiloxane $D_4$. The results can be found in Table 1.

EXAMPLE 10

950 kg of an α,ω-hydroxyl-terminated polydimethylsiloxane having a viscosity of 60 mPas are initially charged in a mixing agitator having a capacity of 2000 l (Becomix RW 2000). The homogenizer is switched on and set to a peripheral speed of 24 m/s. 60 kg of an octyl-decyl phosphate having an acid number of 295 mg KOH/g (obtainable under the "Crodafos 810 A" name from Croda GmbH, D-Nettetal), 100 kg of an ethoxylated lauryl alcohol of the formula $C_{12}H_{23}$—O—$(CH_2CH_2O)_{23}$—H (obtainable under the "Brij 35" name from Croda GmbH, D-Nettetal) and 100 kg of water are added and homogenized for 15 min. A firm gel-like phase was formed, which had a yield point of 1050 Pa. This phase was homogenized for a further 45 min until a particle size of less than 500 nm had been attained. Subsequently, the emulsion was diluted with 900 kg of water within 10 min and stored at 15° C. This emulsion had a pH of 1.3. After 48 h, the emulsion is adjusted to a pH of 7 with triethanolamine. Subsequently, 1.8 kg of preservative based on isothiazolinones (obtainable under the "Kathon CG" name from Acima Chemical Industries Ltd., CH-9471 Buchs/SG) were added.

The emulsion thus obtained is then analyzed for particle size, oil viscosity and the content of octamethylcyclotetrasiloxane $D_4$. The results can be found in Table 1.

TABLE 1

| Example | Particle size D(50) in nm | Oil viscosity in Pas | $D_4$ in % by weight |
|---|---|---|---|
| 1 | 205 | 1790 | <0.05 |
| 2 | 153 | 762 | 0.05 |
| 3 | 143 | 1430 | 0.1 |
| 4 | 175 | 1050 | 0.05 |
| 5 | 162 | 1630 | 0.15 |
| 6 | 116 | 1220 | 0.05 |
| 7 | 154 | 2630 | 0.05 |
| 8 | 214 | 1730 | 0.1 |
| 9 | 174 | 1420 | 0.05 |
| 10 | 156 | 1560 | 0.08 |

All inventive emulsions were very stable; they did not exhibit deposition either in the course of centrifuging (1 h at 2500 g) or in the course of storage over 6 months. The particle size was also unchanged after 28 d at 50° C.

EXAMPLE 11

A shampoo 19:3 is formulated as follows, the individual components being designated according to INCI nomenclature: 0.2 part of guar hydroxypropyltrimonium chloride (obtainable under the N-Hance® 3000 name from Hercules Inc.) is dispersed in 11.98 parts of water. 71.7 parts of sodium laureth sulfate (obtainable under the Genapol® LRO 26.5% name from Clariant GmbH) are stirred in gradually and the mixture is heated to 75° C. In the course of this, 0.3 part of PEG-150 distearate (obtainable under the Emulgin® EO 33 name from Cognis Deutschland GmbH) is added on attainment of 50° C. and, when 65° C. has been attained, 1.2 parts of glycol distearate (obtainable under the Genapol® PMS name from Clariant GmbH). The mixture is mixed until 75° C. has been attained. Then the mixture is cooled. When 35° C. has been attained, 0.06 part of methylchloroisothiazolinone/methylisothiazolinone preservative (obtainable under the Kathon™ CG name from Rohm & Haas Company, Inc.) and 4 parts of the emulsion of example 6 are added and the mixture is stirred for 5 minutes. Finally, 10.06 parts of cocamidopropyl betaine (obtainable under the Genagen® CAB 30% name from Clariant GmbH) and 0.5 part of sodium chloride 25% are added and the mixture is stirred for 10 minutes in each case.

The shampoo thus obtained improves both wet and dry combability, and also the feel of the wet and dry hair.

EXAMPLE 12

A shampoo 11:4 is formulated as follows, the individual components being designated according to INCI nomenclature: 0.1 parts of Polyquaternium-10 (obtainable under the Ucare™ Polymer JR-400 name from Amerchol Corporation) are dispersed in 39.04 parts of water. 41.5 parts of sodium laureth sulfate (obtainable under the Genapol® LRO 26.5% name from Clariant GmbH) are stirred in gradually and the mixture is heated to 75° C. In the course of this, 0.2 part of hydroxyethyl cellulose (obtainable under the Tylose® H 4000 P2 name from Shin-Etsu Chemical Co.) is added on attainment of 50° C. and, when 65° C. has been attained, 1.2 parts of glycol distearate (obtainable under the Genapol® PMS name from Clariant GmbH). The mixture is mixed until 75° C. has been attained. Then the mixture is cooled. When 35° C. has been attained, 0.06 part of methylchloroisothiazolinone/methylisothiazolinone preservative (obtainable under the Kathon™ CG name from Rohm & Haas Company, Inc.) and 4 parts of the emulsion of example 6 are added and the mixture is stirred for 5 minutes. Finally, 13.4 parts of cocamidopropyl betaine (obtainable under the Genagen® CAB 30% name from Clariant GmbH) and 0.5 part of sodium chloride 25% are added and the mixture is stirred for 10 minutes in each case.

The shampoo thus obtained improves both dry and wet combability, and also the feel of wet and dry hair.

EXAMPLE 13

A conditioner is formulated as follows, the individual components being designated according to INCI nomenclature: 87.04 parts of water are initially charged and heated to 75° C. while stirring. In the course of this, 1.2 parts of hydroxyethyl cellulose (obtainable under the Tylose® H 4000 P2 name from Shin-Etsu Chemical Co.) are added. When 65° C. has been attained, 0.5 part of stearamidopropyl dimethylamine (obtainable under the Incromine™ SB name from Croda GmbH), 1 part of Polysorbate 80 (obtainable under the Tween™ 80 name from Croda GmbH), 3 parts of stearyl alcohol (obtainable under the stearyl alcohol name from Merck-Schuchardt), 1 part of cetyl alcohol (obtainable under the cetyl alcohol name from Merck KGaA) and 1.76 parts of behentrimonium chloride (obtainable under the Genamin® KDMP name from Clariant GmbH) are added. The mixture is mixed until 75° C. has been attained. Then the mixture is cooled. During the cooling, 0.2 part of citric acid (obtainable under the citric acid name from Sigma) and 0.2 part of tetrasodium EDTA (obtainable under the EDETA® B powder name from BASF Corporation) are added. When 35° C. has been attained, 0.1 part of methylchloroisothiazolinone/methylisothiazolinone preservative (obtainable under the Kathon™ CG name from Rohm & Haas Company, Inc.) and 4 parts of the emulsion of example 6 are added and the mixture is stirred for 5 minutes. Finally, the mixture is homogenized using the Turrax for 1 minute.

The conditioner thus obtained improves both wet and dry combability, and also the feel of dry and wet hair.

The invention claimed is:
1. An emulsion of polyorganosiloxanes comprising
   (A) at least one polyorganosiloxane having a viscosity greater than 10,000 mm²/s, measured at 25° C.,
   (B) at least one emulsifier of the formula

$$(RO)_n P(O)(OH)_{(3-n)} \quad (I),$$

in which
   R are the same or different and are monovalent hydrocarbyl radicals having 4 to 30 carbon atoms,
   n is 1 or 2,
   and/or salts thereof,
   (C) at least one emulsifier selected from the group consisting of
   (C1) ethoxylated triglycerides having 40 to 400 oxyethylene groups,
   (C2) ethoxylated sorbitan esters of fatty acids having 12 to 18 carbon atoms and 10 to 40 oxyethylene groups,
   (C3) compounds of the formula $$R^1-O-(CH_2CH_2O)_m-H \quad (II)$$

and
   (C4) compounds of the formula $$R^2CH_2C(O)-O-(CH_2CH_2O)_p-H \quad (III),$$

in which
   $R^1$ is a linear alkyl radical having 10 to 30 carbon atoms,
   $R^2$ is an alkyl radical having 10 to 30 carbon atoms,
   m is from 15 to 100 and
   p is from 15 to 100,
   and
   (D) water,
   with the proviso that the emulsion contains less than 2% by weight of octaorganylcyclotetrasiloxane (D$_4$), based on the weight of component (A).

2. The emulsion of claim 1, containing less than 1% by weight of octaorganylcyclotetrasiloxane (D$_4$), based on the weight of component (A).

3. The emulsion of claim 1, wherein the polyorganosiloxane (A) has a viscosity greater than 100,000 mm²/s, measured at 25° C.

4. The emulsion of claim 2, wherein the polyorganosiloxane (A) has a viscosity greater than 100,000 mm²/s, measured at 25° C.

5. The emulsion of claim 1, having a mean volume a particle diameter of 50 to 1000 nm.

6. The emulsion of claim 1, wherein component (C) comprises at least one compound of the formula (II).

7. A process for producing an emulsion of claim 1, comprising: mixing by stirring and/or homogenizing
   (a) polyorganosiloxanes containing units of the formula $$R^4_a(R^3O)_b SiO_{(4-a-b)/2} \quad (IV),$$

in which
   $R^4$ are the same or different and are monovalent, optionally substituted hydrocarbyl radicals having 1 to 30 carbon atoms or hydrogen atom,
   $R^3$ are the same or different and are hydrogen or monovalent, optionally substituted hydrocarbyl radicals,
   a is 0, 1, 2 or 3 and
   b is 0, 1, 2 or 3,
   with the proviso that the sum of a+b is less than or equal to 3, and the polyorganosiloxanes contain 5 to 500 units of the formula (IV), where b is not 0 in at least one unit,
   (b) at least one emulsifier of the formula (I), wherein OH groups of the emulsifier of the formula (I) are optionally partly neutralized,
   (c) at least one emulsifier selected from the group consisting of ethoxylated triglycerides having 40 to 400 oxyethylene groups, ethoxylated sorbitan esters of fatty acids having 12 to 18 carbon atoms and 10 to 40 oxyethylene groups, compounds of the formula (II) and compounds of the formula (III),
   (d) water and optionally
   (e) further substances and condensing the organopolysiloxanes (a) containing units of the formula (IV) at a temperature of from 0 to 50° C. until a desired viscosity has been attained and then the emulsifier of the formula (I) is optionally neutralized with bases such that the pH of the emulsion is greater than 5, and optionally adding further water (d) and/or further substances (e).

8. The process of claim 7, wherein component (c) is used in amounts of 1 to 25 parts by weight, based on 100 parts by weight of polyorganosiloxane (a).

9. The process of claim 7, comprising in a 1st step, mixing and or homogenizing
(a) 100 parts by weight of polyorganosiloxanes containing units of the formula

in which
R$^4$ are the same or different and are monovalent, optionally substituted hydrocarbyl radicals having 1 to 30 carbon atoms or hydrogen,
R$^3$ are the same or different and are hydrogen or monovalent, optionally substituted hydrocarbyl radicals,
a is 0, 1, 2 or 3 and
b is 0, 1, 2 or 3,
with the proviso that the sum of a+b is less than or equal to 3, and the organopolysiloxanes contain 5 to 500 units of the formula (IV), where b is not 0 in at least one unit, with
(b) 1 to 30 parts by weight of at least one emulsifier of the formula (I), wherein OH groups of the emulsifier of the formula (I) are optionally partly neutralized,
(c) 1 to 30 parts by weight of at least one emulsifier selected from the group consisting of ethoxylated triglycerides having 40 to 400 oxyethylene groups, ethoxylated sorbitan esters of fatty acids having 12 to 18 carbon atoms and 10 to 40 oxyethylene groups, compounds of the formula (II) and compounds of the formula (III),
(d) 1 to 50 parts by weight of water and optionally,
(e) further substances;
in an optional 2nd step
adding further water (d);
in a 3rd step
condensing the organopolysiloxanes(s) (a) containing units of the formula (IV) at a temperature of from 0 to 50° C. until a desired viscosity has been attained;
in an optional 4th step
neutralizing the emulsifier(s) of the formula (I) is are with base such that the pH of the emulsion is greater than 5, and
in an optional 5th step
mixing the emulsion obtained in the 4th step with further water (d) and/or further substances (e).

10. A personal care composition comprising an emulsion of claim 1 in an amount of from 0.05 to 10% by weight.

11. A personal care composition comprising an emulsion produced by the process of claim 7, in an amount of from 0.05 to 10% by weight.

12. A personal care composition comprising an emulsion produced by the process of claim 9, in an amount of from 0.05 to 10% by weight.

13. The personal care composition of claim 10, which is a haircare composition, further comprising at least one conditioner.

14. The personal care composition of claim 11, which is a haircare composition, further comprising at least one conditioner.

15. The personal care composition of claim 12, which is a haircare composition, further comprising at least one conditioner.

* * * * *